Figure 1:
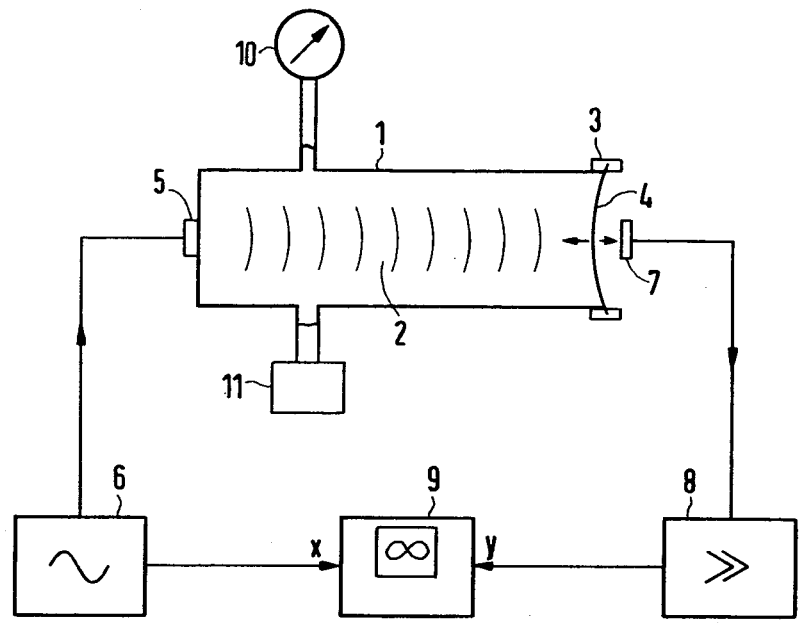

United States Patent [19]
Vogt

[11] 4,455,871
[45] Jun. 26, 1984

[54] METHOD AND APPARATUS FOR THE NON-DESTRUCTIVE MEASUREMENT OF THE RESPONSE PRESSURE OF REVERSIBLE RUPTURE DISCS

[75] Inventor: Peter Vogt, Rösrath, Fed. Rep. of Germany

[73] Assignee: INTERATOM Internationale Atomreaktorbau GmbH, Bergisch-Gladbach, Fed. Rep. of Germany

[21] Appl. No.: 400,589

[22] Filed: Jul. 21, 1982

[30] Foreign Application Priority Data

Jul. 29, 1981 [DE] Fed. Rep. of Germany ....... 3129998

[51] Int. Cl.³ .................... G01H 13/00; G01N 3/36; G01L 9/00
[52] U.S. Cl. .................................. 73/579; 73/840
[58] Field of Search ............. 73/579, 812, 852, 853, 73/702, 838, 840, 37

[56] References Cited

U.S. PATENT DOCUMENTS 3,290,922 12/1966 Thompson ................... 73/579 X
4,170,141 10/1979 Woo ............................. 73/812 X

*Primary Examiner*—James J. Gill
*Attorney, Agent, or Firm*—Herbert L. Lerner; Laurence A. Greenberg

[57] ABSTRACT

Method of non-destructively determining response pressure of a reversible rupture disc which includes: measuring resonance frequencies of lower vibration modes of the reversible rupture disc at varying measuring pressures below the response pressure of the reversible rupture disc; and extrapolating from the resonance frequencies of each of the vibration modes as a function of the measuring pressure, that pressure at which the resonance frequency of the respective vibration mode becomes zero, the lowest pressure at which one of the vibration modes would have zero resonance frequency being the lowest response pressure of the reversible rupture disc; and apparatus for performing the method.

16 Claims, 2 Drawing Figures

METHOD AND APPARATUS FOR THE NON-DESTRUCTIVE MEASUREMENT OF THE RESPONSE PRESSURE OF REVERSIBLE RUPTURE DISCS

The invention relates to a method and apparatus for the non-destructive measurement of the response pressure of reversible rupture discs.

The use of reversible rupture discs as safety valves, which abruptly release or open a large cross section if a given pressure is exceeded, is widely known. Of particular interest in this regard is having the most accurate knowledge possible of the response pressure at which the destruction occurs. A method of measuring the response pressure, particularly also for built-in reversible rupture discs, has not been known heretofore. The method used heretofore for determining the response pressure calls for making a given number of reversible rupture discs as exactly alike as possible and testing a given percentage thereof destructively. From the response pressures of the destroyed reversible rupture discs, conclusions are then drawn as to the remainder of the series. With this heretofore known procedure, the number of destroyed discs is either very large or the tolerance of the indicated response pressure is very large. The information obtained is, furthermore, only of a statistical nature and cannot take individual differences into account. The method used heretofore is therefore expensive, on the one hand, and the result for individual reversible rupture discs is unsatisfactory, on the other hand.

It is an object of the invention, therefore, to provide a method and apparatus for non-destructive measurement of the response pressure of reversible rupture discs wherein it is possible to determine within a very small tolerance the response pressure for each individual rupture disc, especially also for rupture discs which have already been built-in at the final location thereof. It is a further object to provide such a method and apparatus by which in-service tests which allow conclusions as to material fatigue and the like are rendered possible. It is yet another object of the invention to provide such a method and apparatus as will make possible the trimming of the response pressure, in conjunction with this method of non-destructive testing, especially also through changes in the clamping or by targeted machining.

With the foregoing and other objects in view, there is provided, in accordance with the invention, a method of non-destructively determining response pressure of a reversible rupture disc which comprises: measuring resonance frequencies of lower vibration modes of the reversible rupture disc at varying measuring pressures below the response pressure of the reversible rupture disc; and extrapolating from the resonance frequencies of each of the vibration modes as a function of the measuring pressure, that pressure at which the resonance frequency of the respective vibration mode becomes zero, the lowest pressure at which one of the vibration modes would have zero resonance frequency being the lowest response pressure of the reversible rupture disc.

For a better understanding of the foregoing method according to the invention, the pertinent theory is briefly explained as follows:

In the method, the unstable bulging upon response of the rupture disc is considered as a special case of free vibration of the rupture disc dome. A vibration is characterized by the fact that an excursion or deflection A from rest position is counteracted by a restoring force K. Simplified, the frequency f depends upon the relationship $f^2 = \text{const } K/A$.

The restoring force K, in the general case, is made up partly of elastic-material deformation and partly of external load, which may be positive or negative. A positive contribution of the external load signifies that the load counteracts the deflection which is usually connected with tensile stress. A negative contribution to the restoring force indicates that the external load aids the deflection, which is usually connected with compression stress. A positive contribution of the external load to the restoring force increases the frequency of the free vibration, and a negative contribution lowers the frequency. In an extreme case, the negative contribution lowers the frequency to the point where no restoring force is present anymore. In this extreme case, the vibration frequency is zero. For such a case, the system must be classed as unstable, since there is no longer any restoring force: a kink or bulge is produced, which leads to rupture.

The fact that the frequency of the free vibration for this extreme case of unstable failure is known ($f = 0$) permits the drawing of conclusions from the frequency response as a function of the pressure in the non-critical load range on the load at failure, in accordance with the method of the invention.

It can be shown that the restoring force and, thereby, the square of the vibration frequency is linear with respect to the external load, in any case for small deformations and stresses below the proportionality limit. These conditions are sufficiently met in reversible rupture discs. In case this should not be true in particular or special cases, corrective measures must be provided in determining the response pressure.

The application is made more difficult only by the fact that the domed rupture disc has several vibration modes which vibrate with varying frequency and the frequency of which varies to different extents with the internal pressure. However, there is always linearity of the dependence. The vibration mode which corresponds to the mode of failure is of importance for the response pressure. This vibration mode is the one which attains the frequency zero with the lowest internal pressure. In a rupture disc wherein the vibration mode for the failure case is not known, the dependence of the frequency upon the internal pressure must be determined for different vibration modes and must, respectively, be extrapolated linearly down to the zero point. In practice, however, this requires only an examination of the four lowest vibration modes, because higher vibration modes are not likely to be failure modes. Frequently, it is the second vibration mode which leads to failure.

In carrying out the method, care must therefore be taken that the correlation of the measuring points to the respective vibration mode be correctly performed because, otherwise, misinterpretations will occur. A suitable procedure for performing the measuring is described hereinafter. For now it is important that for each measured pressure, several resonances of the reversible rupture disc vibration must be ascertained in accordance with the different vibration modes. As mentioned hereinbefore, it is sufficient to seek out the lowest four resonances. With measurements taken for at least three different pressures sufficiently far apart, the results may already be unambiguously interpretable; measuring accuracy may be increased, of course, by suitable selection of the number of measuring points and measuring pressures.

In accordance with another and especially significant feature of the invention, the reversible rupture disc is in the final built-in state thereof. This, on the one hand, makes it possible to perceive installation influences or effects and, on the other hand, in-service tests and, if necessary or desirable, measures for trimming the response pressure are possible.

In accordance with alternate features of the invention, the reversible rupture disc is excited to vibrations in built-in condition thereof at different measuring pressures, by being struck or by being driven with noise of a sound emitter. The vibration is recorded by a microphone or a suitable vibration pickup, and the frequency spectrum of the vibration is analyzed. In this manner, the resonance frequencies of the different vibration modes are found.

In accordance with a further feature of the invention wherein a somewhat more exact method is provided, the vibrations of the reversible rupture disc are generated by a sound emitter which is driven by a frequency generator. A vibration pick-up then registers the amplitude of the vibration of the reversible rupture disc, while the frequency at the frequency generator is varied continuously. Resonance frequencies are determined by the fact that the amplitude of the vibration assumes a maximum.

In accordance with yet another feature of this more exact method of the invention, the sound is transmitted, via the structure of the apparatus for performing the method, to the reversible rupture disc. This has the advantage that the sound emitter does not have to be coupled with the fluid, which would lead to difficulties under certain conditions in previously existing installations.

On the other hand, however, it may also be of advantage to transmit the sound via the fluid to the reversible rupture disc, especially if the structure is not suitable for transmitting sound. In such a case, the sound emitter is coupled with the liquid, and the sound is then transmitted to the reversible rupture disc.

In order to minimize the influence or effect of the measuring equipment on the vibration of the reversible rupture disc to the greatest extent possible, in accordance with an added feature of the invention, the vibration is measured without making contact. Inductive or capacitive techniques are suitable therefor. Since reversible rupture discs are very sensitive, and external influences should be eliminated in the measurement, this feature or mode of the method is preferable to any fastening of measuring devices.

In accordance with an additional mode of the method invention, the resonance frequencies can be identified without great expenditure for apparatus. For this purpose, the electron beam of an oscilloscope is driven in the one coordinate of a rectangular coordinate system, for example, by the output of the frequency generator and, in the second coordinate, by the amplitude of the vibration of the reversible rupture disc. If the frequency of the sound emitter is then varied continuously, so-called Lissajous figures are produced on the oscilloscope, which make direct identification of the vibration modes and the resonance frequencies possible. The resonance frequencies found for a given measuring pressure can then be introduced into a diagram (note hereinafter the explanation in connection with FIG. 2), whereby a graphic determination of the response pressure is facilitated.

In accordance with yet a further feature of the invention, apparatus for implementing the method of the invention is provided. A reversible rupture disc is built into a structure by means of a mount in a manner that it separates from the surroundings a fluid received in the interior of the structure. The fluid may be pressurized by means of a pump or similar device; the pressure may also be read by means of a measuring device. By means of suitable devices, the reversible rupture disc can be set into vibration, and the resulting vibrations can be measured and the resonance frequencies determined by suitable means. In a previously built-in rupture disc, the structure, mounting and pressure measuring device are usually already provided, so that only the remaining means must be attached.

In accordance with alternative features of the invention, the sound emitter is disposed on the structure or the sound emitter is acoustically coupled with the fluid. Both possibilities are suitable, depending upon equipment factors, for setting the rupture disc in vibration.

In accordance with yet an added feature of the invention, a contactless sensor is employed as the vibration measuring device, whereas, for the case wherein the outside of the reversible rupture disc is not accessible, the vibration pick-up can also be fastened to the structure in the proximity of the reversible rupture disc. In many cases, a reversible rupture disc only separates two sections of a tube, so that no sensor can be attached in the vicinity of the rupture disc dome. For such a case, a vibration measurement is provided via the structure whereby then, excitation of the vibration should occur logically via the fluid.

In accordance with another feature of the invention, means are provided for measuring resonance frequencies by means of Lissajous figures.

In accordance with a concomitant feature of the invention, the apparatus includes a sound emitter and a sound pick-up together with auxiliary equipment provided as a transportable unit, the sound emitter and vibration measuring device being disposable on different structures. By means of such a device, a rupture disc already installed in any structure can be examined for the response pressure thereof. The sound emitter and the sound pick-up are merely mounted at suitable locations and the examination is then carried out as described.

Other features which are considered as characteristic for the invention are set forth in the appended claims.

Although the invention is illustrated and described herein as embodied in a method and apparatus for the non-destructive measurement of the response pressure of reversible rupture discs, it is nevertheless not intended to be limited to the details shown, since various modifications and structural changes may be made therein without departing from the spirit of the invention and within the scope and range of equivalents of the claims.

Figure 2:
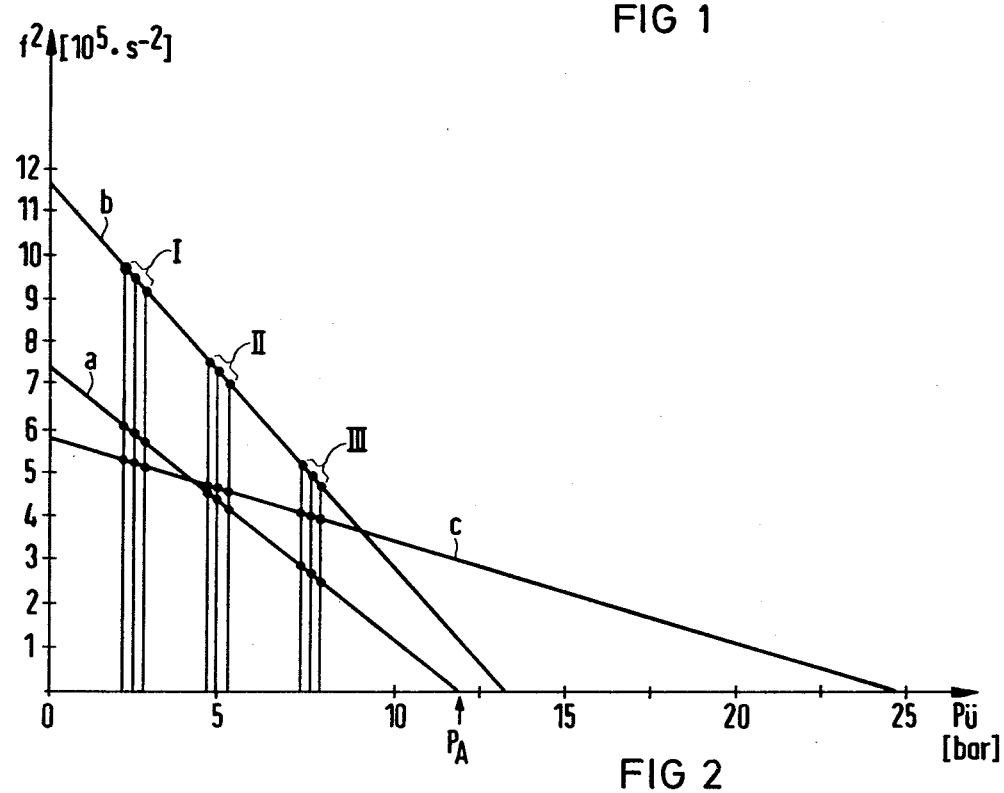

The construction and method of operation of the invention, however, together with additional objects and advantages thereof will be best understood from the following description of specific embodiments in connection with the accompanying drawings, in which:

FIG. 1 is a diagrammatic and schematic view of a device for nondestructive determination of the response pressure of reversible rupture discs according to the invention; and FIG. 2 is a plot diagram such as is obtained in recording the measurement values together with graphic extrapolations thereof.

Referring now to the drawing and, first, particularly to FIG. 1 thereof, there is shown a structure which, in the simplest case, is a tube of suitable diameter. In the interior of this structure, a fluid 2 is received. By means of a suitable mounting or holder 3, a reversible rupture disc 4 is attached. At a suitable location of the structure 1, a sound generator 5 is fastened which is either coupled acoustically to the fluid or transmits the sound generated thereby via the structure 1 to the rupture disc 4. A frequency generator 6 drives the sound generator 5, and a preferably contactless sensor 7 is mounted closely in front of the reversible rupture disc 4. The sensor 7 may also be an inductive or capacitive sensor. An amplifier 8 amplifies the received signals and passes it on to the y-input of an oscilloscope 9. The x-input of the oscilloscope 9 is connected to the output of the frequency generator 6. Lissajous figures are produced on the oscilloscope and afford identification of resonances when both the x and y inputs are driven simultaneously. Since the measuring is to be peformed for varying fluid pressures, a pressure gauge 10 is provided as well as a device 11 for adjusting or setting the desired pressure, such as a pump, for example. Usually, apparatus in which reversible rupture discs are used already has suitable means for setting and reading the pressure, so that only a sound emitter and a vibration sensor need be attached thereto. In this manner, rupture discs already built-in at the place of destination thereof can be examined.

In FIG. 2, a diagram is shown such as is generated by graphically evaluating measurements or tests performed in accordance with proposed method. Pressure is plotted along the x-axis, and the square of the frequency along the y-axis. In this way, the desired functional relationship is represented as a straight line. Straight lines a, b and c represent the frequency dependency on the system pressure for the lowest three vibration modes. It is apparent that these straight lines a, b and c can intersect within the measuring range, so that it may not be quite so simple, under certain circumstances, to correlate the measuring points correctly. While, in principle, three measuring points at different pressures should be sufficient when the measuring accuracy is high, difficulties may be encountered, however, if one of the measuring points should happen to be in the vicinity of an intersection. It is therefore proposed, as indicated in FIG. 2, to record at least three measuring groups I, II and III, in order to attain a reliable interpretation of the measuring points and a correlation with the corresponding vibration modes. In this manner, enough measuring points are generated for an exact fixation or establishment of each straight line, and the measuring points can also be extrapolated, into the range of the response pressure with sufficient accuracy. That straight line which intersects the x-axis at the lowest pressure, corresponds to the failure vibration mode. The intersection with the x-axis indicates the exact response pressure $P_A$. In the diagram of FIG. 2, the straight lines for higher vibration modes would all run higher, for which reason they play no part any longer in the investigation of the response pressure. In the interest of greater simplicity and clarity, only a graphic evaluation method has been described herein. Of course, a numerical and possibly computer-aided evaluation is always possible also. In this case, the straight line would be calculated from the measuring points by means of one of the conventional equalization methods and the intersection point with the x-axis would be established.

The method explained herein therefore offers, in principle, the possibility of measuring non-destructively, with a tolerance almost as small as desired, the response pressure for an individual rupture disc. By increasing the number of measuring points and expanding the measuring range, the accuracy can, in any event, far exceed what has been possible heretofore by statistical methods and destructive tests.

I claim:

1. Method of non-destructively determining response pressure of a reversible rupture disc which comprises: measuring resonance frequencies of lower vibration modes of the reversible rupture disc at varying measuring pressures below the response pressure of the reversible rupture disc; and extrapolating from the resonance frequencies of each of the vibration modes as a function of the measuring pressure, that pressure at which the resonance frequency of the respective vibration mode becomes zero, the lowest pressure at which one of the vibration modes would have zero resonance frequency being the lowest response pressure of the reversible rupture disc.

2. Method according to claim 1, wherein the reversible rupture disc is in the final built-in state thereof.

3. Method according to claim 1, which comprises striking the reversible rupture disc to effect vibration thereof; and analyzing the frequency spectrum of the vibration.

4. Method according to claim 1, which comprises applying sound from a sound emitter to the reversible rupture disc to effect vibration thereof; and analyzing the frequency spectrum of the vibration.

5. Method according to claim 1, which comprises generating the vibrations of the reversible rupture disc by means of a sound emitter; driving the sound emitter by a frequency generator with continuously variable frequency; and registering the amplitude of the vibration of the reversible rupture disc with a vibration pick-up.

6. Method according to claim 5, wherein the sound is transmitted to the reversible rupture disc via the structure of apparatus for performing the method.

7. Method according to claim 5, wherein the sound is transmitted to the reversible rupture disc through a fluid.

8. Method according to claim 5, wherein measuring of the vibration of the reversible rupture disc is contactless.

9. Method according to claim 5, wherein the vibration of the sound emitter determines the deflection of an electron beam of an oscilloscope in one coordinate of a rectangular coordinate system; and the vibration of the reversible rupture disc determines the deflection of the electron beam in the other coordinate of the rectangular coordinate system; and which includes continuously varying the frequency of the sound emitter; the respective deflections of the electron beam in the two coordinates forming Lissajous figures in the oscilloscope whereby the vibration modes and resonance frequencies are identifiable.

10. Apparatus for nondestructively determining response pressure of a reversible rupture disc comprising a structure having a holder for clampingly mounting the reversible rupture disc; a fluid disposed within said structure; means for varying the pressure of said fluid;

means for measuring the pressure of said fluid; means for exciting vibration of the reversible rupture disc; means for measuring vibrations of the reversible rupture disc; and means for determining resonance frequencies of the vibrations of the reversible rupture disc.

11. Apparatus according to claim 10, wherein said vibration exciting means are a sound emitter disposed on said structure.

12. Apparatus according to claim 10, wherein said vibration exciting means are a sound emitter acoustically coupled with said fluid.

13. Apparatus according to claim 10, wherein said vibration measuring means are a contactless sensor.

14. Apparatus according to claim 10, wherein said vibration measuring means are a vibration pick-up device fastened to said structure in vicinity of the reversible rupture disc.

15. Apparatus according to claim 10, wherein said means for determining resonance frequencies are an oscilloscope; said vibration exciting means are a frequency generator having an output connected to an x-input of said oscilloscope; and said vibration measuring means are connected via an amplifier to a y-input of said oscilloscope.

16. Apparatus according to claim 10, wherein the reversible rupture disc is in the final built-in state thereof, and wherein said vibration exciting means and said vibration measuring means are, respectively, a sound emitter and a sound pick-up unit which, together with auxiliary equipment, are formed as a transportable unit, said sound emitter and said sound pick-up unit being disposable on different structures.

* * * * *

UNITED STATES PATENT AND TRADEMARK OFFICE
CERTIFICATE OF CORRECTION

PATENT NO. : 4,455,871
DATED : June 26, 1984
INVENTOR(S) : PETER VAGT

It is certified that error appears in the above-identified patent and that said Letters Patent are hereby corrected as shown below:

In the heading, item (75), line 7,

"Peter Vogt"

should read

--Peter Vagt--.

Signed and Sealed this

Twenty-fourth Day of February, 1987

Attest:

DONALD J. QUIGG

Attesting Officer    Commissioner of Patents and Trademarks